(12) United States Patent
Martin et al.

(10) Patent No.: US 7,547,456 B2
(45) Date of Patent: Jun. 16, 2009

(54) COMPOSITION CONTAINING FEVERFEW EXTRACT AND USE THEREOF

(75) Inventors: Katharine M. Martin, Ringoes, NJ (US); Claude Saliou, Bernardsville, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 10/099,159

(22) Filed: Mar. 14, 2002

(65) Prior Publication Data

US 2002/0182166 A1    Dec. 5, 2002

Related U.S. Application Data

(60) Provisional application No. 60/276,304, filed on Mar. 16, 2001.

(51) Int. Cl.
  *A61K 36/28* (2006.01)
  *A61K 8/02* (2006.01)
  *A61K 33/00* (2006.01)
  *A61K 36/00* (2006.01)

(52) U.S. Cl. ............... 424/764; 424/401; 424/724; 424/725

(58) Field of Classification Search ............. 424/195.1, 424/764, 724, 725, 401
See application file for complete search history.

(56) References Cited

U.S. PATENT DOCUMENTS

| | | | |
|---|---|---|---|
| 3,755,560 A | 8/1973 | Dickert et al. | |
| 4,096,240 A | 6/1978 | Mathur | |
| 4,254,105 A | 3/1981 | Fukuda | |
| 4,268,629 A | 5/1981 | Tolbert et al. | |
| 4,421,769 A | 12/1983 | Dixon et al. | |
| 4,593,038 A * | 6/1986 | Burzynski | 514/328 |
| 4,758,433 A | 7/1988 | Johnson et al. | |
| 4,959,205 A * | 9/1990 | Brunner et al. | 424/59 |
| 4,960,764 A | 10/1990 | Figueroa, Jr. et al. | |
| 5,260,065 A | 11/1993 | Mathur et al. | |
| 5,268,176 A | 12/1993 | Znaiden et al. | |
| 5,550,148 A | 8/1996 | West et al. | |
| 6,103,218 A | 8/2000 | Brucker et al. | |
| 6,130,254 A | 10/2000 | Fisher et al. | |
| 6,153,208 A | 11/2000 | McAtee et al. | |
| 6,190,664 B1 | 2/2001 | Dampeirou | |
| 6,224,875 B1 * | 5/2001 | Bombardelli et al. | 424/764 |
| 6,410,062 B1 | 6/2002 | Callaghan et al. | |
| 6,479,080 B2 | 11/2002 | Bombardelli et al. | |
| 6,620,419 B1 | 9/2003 | Lintner | |
| 2001/0021400 A1 | 9/2001 | Bombardelli et al. | |
| 2002/0182166 A1 | 12/2002 | Martin et al. | |
| 2003/0003170 A1 | 1/2003 | Callaghan et al. | |
| 2003/0077343 A1 | 4/2003 | Martin et al. | |

FOREIGN PATENT DOCUMENTS

| | | |
|---|---|---|
| DE | 198 501 | 7/1958 |
| EP | 0 427 411 A2 | 5/1991 |
| EP | 0 273 202 B1 | 6/1995 |
| JP | 8225428 A | 9/1996 |
| JP | 11035444 A | 2/1999 |
| JP | 2000143485 A | 5/2000 |
| WO | WO 94/06800 A1 | 3/1994 |
| WO | WO 96/31194 A2 | 10/1996 |
| WO | WO 97/02807 * | 1/1997 |
| WO | WO 97/02807 A1 | 1/1997 |
| WO | WO 00/74695 A2 | 12/2000 |
| WO | WO 00/74699 * | 12/2000 |
| WO | WO 00 74699 A1 | 12/2000 |
| WO | WO 00/74699 A1 | 12/2000 |
| WO | WO 02/074280 A1 | 9/2002 |

OTHER PUBLICATIONS

Hausen et al., abstract ,Contact allergy to parthenolide in Tanacetum parthenium . . . , 1983.*
PCT Search Report for PCT/US02/07970 dated Aug. 5, 2002.
Johnson, Timothy, CRC Ethnobotany Desk Reference, CRC Press, NY, 1999, pp. 198-199,516-517,823-824.
International Plant Names Index published on the Internet, http://www.ipni.org.
Connor, Michael, Wheeler, Larry, Depletion of Cutaneous Glutathione by Ultraviolet Radiation, Photochemistry and Photobiolgy, 1987, vol. 46, No. 2, pp. 239-245.
Fisher, Gary J., Voorhees, John J., Molecular Mechanisms of Photoaging and its Preventions by Retinoic Acid: Ultraviolet irradiation Induces MAP Kinase Signal Transduction Cascades that Induce AP-1-Regulated Matrix Metalloproteinases that Degrade Human Skin In Vivo, The Society for Investgative Dermatology, Inc. 1998pp. 61-68.
Fisher, Gary J. , Subhash C. Datta, Harvinder S. Talwar, Zeng-Quan Wang, James Varani, Sewon Kang and Voorhees, John J., Nature, 1996, vol. 379, pp. 335-339.
Hanada, Katsumi, Sawamura, Daisuke, Tamai, Katsuto, Hashimoto, Isao, Kobayahi, Shizuko, Photoprotective Effect of Esterified Glutathione Against Ultraviolet B-Induced Sunburn Cell Formation in the Hairless Mice, The Society for Investigative Dermatology, Inc. 1997, pp. 727-730.

(Continued)

*Primary Examiner*—Jennifer M Kim

(57) ABSTRACT

The present invention features a composition for regulating the firmness, tone, or texture of skin, or for regulating wrinkles, or for the treatment of external aggression in skin containing a safe and effective amount of a Feverfew extract and a cosmetically-acceptable topical carrier, and the use thereof.

13 Claims, No Drawings

OTHER PUBLICATIONS

Hausen, B.M. and Schulz, K.H., Chrysanthemum Allergy, Arch. Derm. Res. 1976, vol. 255,pp. 111-121.

Menage, H.Dup., Ross, J.S., Norris, P.G. Hawk, J.L.M., White I.R., Contact and Photocontact Sensitization in Chronic Actinic Dermatitis: Sesquiterpene Lactone Mix is an Important Allergen, British Journal of Dermatology, 1995:132:543-547.

Meister, Alton, Glutathione, Ascorbate, and Cellular Protection, Cancer Research Suppl, 54, 1994,pp. 1969s-1975s.

Mezei, Michael, Liposomes as a Skin Drug Delivery System, Elsevier Science Publishers, NY, 1985,pp. 345-358.

Mezei, Michael, Gulasekharam, Vijeyalakshmi, Liposomes-A Selective Drug Delivery System for the Topical Route of Administration: Gel Dosage Form, J. Pharm. Pharmacol, 1982,34:473-474.

Orion, E., Paulsen, E. ,Andersen, K.E., Menne T. , Comparison of Simultaneous Patch Testing with Parthenolide and Sesquiterpene Lactone Mix, Contact Dermatitis 1998,38:207-208.

Spettoli, Elisa, Silvani, Simonetta, Lucente, Pasquale, Guerra, Liliana, Vincenzi, Colombina, Contact Dermatitis Caused by Sesquiterpene Lactones, American Journal of Contact Dermatitis, vol. 9, No. 1, 1998:pp. 49-50.

Schulz,K.H., Hausen, B.M., Wallhofer, Schmidt-Loffler, P., Chrysanthemem-Allergic, Arch. Derm. Forsch, 1975,251:pp. 235-244.

Steenvoorden, David, Hasselbaink, Danny, Beijersbergen Van Henegouwen, Gerard M.J., Protection Against UV-Induced Reactive Intermediates In Human Cells And Mouse Skin By Glutathione Precursors: A Comparison Of N-Acetylcystein And Glutathione Ethylester, Photochemistry and Photobiology, 1998,67(6):pp. 651-656.

Tyrrell, R.M., Pidoux, M., Correlation Between Endogenous Glutathione Content and Sensitivity of Cultured Human Skin Cells to Radiation at Defined Wavelengths in the Solar Ultraviolet Range, Photochemistry and Photobiology, 1998, vol. 47, No. 3, ppd. 405-412.

Van Den Broeke, Leon T., Beijersbergen Van Henegouwen, Gerard, M. J., Topically applied N-acetylcysteine as a protector against UVB-induced systemic immunosuppression, Journal of Photochemisty and Photobiology, B: Biology 27, 1995:pp. 61-65.

Sagarin, Edward and Balsam, M.S., Cosmetics Science and Technology, Second Edition, vol. 1, (1972) pp. 32-43.

Wenninger, John A., McEwen, G.N. Jr., International Cosmetic Ingredient Dictionary and Handbook, Seventh Edition (1997)vol. 2, The Cosmetic, Toiletry, and Fragrance Association, Washington, DC, pp. 1626, 1650-1667, 1654-1661, 1693-1697, 1673-1686.

Barsby, R.W.J. Salan, Umit, Night, D.W., Hoult, J.R.S., Feverfew and Vascular Smooth Muscle: Extracts from Fresh and Dried Plants Show Opposing Pharmacological Profiles, Dependent upon Sesquiterpene Lactone Content, Planta Med. 59(1993) pp. 20-25.

Lamminpaa, Anne, Estlander Tuula, Jolanki, Rhtta, Kanerva, Lasse, Occupational allergic contact dermatitis caused by decorative plants, Contact Dermatitis, 1996, 34:pp. 330-335.

XP002147441, Biosis: Biosciences Information Service, Barasby R.W.J. et al.:Philadelphia, PA 1993.

Derwent English abstract of HU 210294B (1995).

Titheradge, Michaela., The Enzymatic Measurement of Nitrate and Nitrite, Methods in Molecular Biology, vol. 100, publicly available prior to Mar. 1, 2002, pp. 83-91.

Detmar, Michael, The Role of VEGF and thrombospondins in skin agiogenesis, Journal of Dermatological Science, 24 Suppl, 1 (2000)S78-S84.

Kollias, N., Baqer, A. Sadiq, i. Sayre, R.M., In vitro And in vivo Ultraviolet-Induced Alterations of Oxy-And Deoxyhemoglobin, Photochemistry and Photobiology vol. 56, No. 2, (1991) pp. 223-227.

Guy, R.H. and Maibach, H.I., Rapid Radial Transport of Methyl Nicotinate in the Dermis, Arch Dermatol Res (1982)273:91-95.

Yancopoulos, George D., Davis, Samuel, Gale, Nicholas W., Rudge, John S., Wiegand Stanley J., Holash, Jocelyn, Vascular-specific growth factors and blood vessel formation, Nature, vol. 407, (2000)pp. 242-248.

Bikfalvi, Andreas, Klein, Sharon, Pintucci, Giuseppe, Rifkin, Daniel B., Biological Roles of Fibroblast Growth Factor-2*, Endocrine Reviews, vol. 18, No. 1, pp. 26-45.

Gerber, Hans-Peter, McMurtrey, Amy, Kowalski, Joe, Yan, Minhong, Keyt, Bruce A, Dixit, Vishva, Ferara, Napoleone, Vascular Endothelial Growth Factor Regulates Endothelial Cell Survival through the Phosphatidylinositol 3'-Kinase/Akt Signal Transduction Pathway, The Journal of Biological Chemistry, (1998), vol. 273,No. 46, pp. 30336-30343.

McCutcheon's Emulsifiers & Detergents, 1986 (North Edition), McPublishing Co., Glen Rock, NJ, pp. 317-324.

Barel, A.O., Courage, W. Clarys, P. , Suction Method for Measurement of Skin Mechanical Properties:The Cutometer®, Handbook of Non-Invasive Methods and the Skin, eds. J. Serup & G. Jemec. Chapter 14.3(1995) pp. 335-340.

Johnson & Johnson Consumer Companies, Inc., Pending U.S. Appl. No. 10/237,389.

Johnson & Johnson Consumer Companies, Inc., Pending U.S. Appl. No. 10/139,498.

International Search Report dated Sep. 9, 2002, for PCT/US03/28032.

Abstract, Acta Derm Venereol 1983:63(4):308-14, Contact allergy to parthenolide in Tanacetum parthenium (L.) Schulz-Bip. (feverfew, Asteraceae)and cross-reactions to related sesquiterpene lactone containing Compositae species.

Jain NK, Kulkarni SK (1999) Antinociceptive and anti-inflammatory effects of *Tanacetum parthenium* L. extracts in mice and rats. J. Ethnopharmacol 68:251-259.

Kwok BH, Koh B, Ndubuisi MI, Elofsson M, Crews CM (2001) The anti-inflammatory natural product parthenolide from the medicinal herb Feverfew directly binds to and inhibits IKappaB kinase. Chem Biol 8:759-766.

Hausen MB, Osmundsen PE (1983) Contact allergy to parthenoilide in *Tanacetum parthenium* (L.) schilz-Bip. (feverfew, Asteraceae) and cross-reactions to related sesquiterpene lactone containing Compositae species. Acta Derm Venereol 63:308-314.

Paulsen E, Christensen LP, Andersen KE (2007) Compositae dermatitis from airborne parthenolide. Br. J Dermatol 156:510-515.

*Physician's Desk Reference*, PDR 57 Edition 2003, pp. 2446-2447.

Sunagawa et al., *Nippon Eisigaku Zasshi*, Jul. 2001, 56(2):500-513 (abstract).

Walther, *Arch Toxicol*, Jul. 2004, 78(7):402-409 (abstract).

* cited by examiner

COMPOSITION CONTAINING FEVERFEW EXTRACT AND USE THEREOF

CROSS REFERENCE TO RELATED APPLICATIONS

This application claims priority from U.S. Ser. No. 60/276,304 filed Mar. 16, 2001, which is incorporated by reference.

FIELD OF THE INVENTION

The present invention relates to compositions comprising Feverfew extract and the cosmetic use thereof.

BACKGROUND OF THE INVENTION

Tanacetum parthenium, a plant commonly known as feverfew, has been recognized since the Middle Ages as having significant medicinal properties when taken orally as a general febrifuge, hence its common name. Many have isolated extracts of this plant, and those extracts have been used to orally treat migraines, arthritis, and bronchial complaints. See, e.g., U.S. Pat. No. 4,758,433 and PCT Patent Application No. WO 94/06800.

Extracts of feverfew contain many components. Although not all components have been isolated and characterized, the known components of an extract of feverfew contain a significant number of biologically active components. To date, the chemical constituents of whole feverfew extract include, but are not limited to, apigenin-7-glucoside, apigenin-7-glucuronide, 1-β-hydroxyarbusculin, 6-hydroxykaempferol-3,7-4'-trimethylether (Tanetin), 6-hydroxykaempferol-3,7-dimethyl ether, 8-β-reynosin, 10-epicanin, ascorbic acid, beta-carotene, calcium, chromium, chrysanthemolide, chrysanthemomin, chrysarten-A, chrsyarten-c, chrysoeriol-7-glucuronide, cobalt, cosmosiin, epoxyartemorin, luteolin-7-glucoside, luteolin-7-glucuronide, mangnoliolide, parthenolide, quercetagentin-3,7,3,-trimethylether, quercetagetin-3'7-dimethylether, reynosin, tanaparthin, tanaparthin-1α,4α-epoxide, tanaparthin-1β,4β-epoxide, β-costunolide, 3-β-hydroxy-parthenolide, and 3,7,3'-trimethoxyquercetagetin.

The specific role that each of these component compounds plays in the biological activity of feverfew, however, is to date unknown. Some information, however, is known about the allergic reactions to the extract. It is believed that many of these allergic reactions are caused by the alpha-unsaturated gamma-lactones such as parthenolide. See, e.g., Arch. Dermatol. Forsch. 1975, 251 (3):235-44; Arch. Dermatol. Forsch 1976, 255 (2):111-21; Contact Dermatitis, 1988, 38 (4):207-8; Am. J. Contact Dermatol. 1998-9 (1):49-50; and Br. J. Dermatol, 1995, 132 (4): 543-47.

While there are reports that parthenolide may be useful for inhibiting photoaging of skin, see U.S. Pat. No. 6,130,254, there are no teachings which describe the use of an extract of feverfew with reduced amounts of the allergy causing alpha-unsaturated gamma-lactones for regulating skin aging factors or for treating and preventing environmental damage or external aggressions.

SUMMARY OF THE INVENTION

In one aspect, the invention features a composition for regulating skin aging factors such firmness, tone, or texture of skin or regulating wrinkles in skin containing a feverfew extract and a cosmetically-acceptable topical carrier. In one embodiment, the composition is substantially free of alpha-unsaturated gamma-lactones.

In another aspect, the invention features a composition for the treatment of external aggressions in skin including Feverfew extract and a cosmetically-acceptable topical carrier. In another aspect, the present invention also features the use of such compositions.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

Definitions

As used herein, "topical application" means directly laying on or spreading on outer skin using, e.g., by use of the hands or an applicator such as a wipe.

As used herein, "cosmetically-acceptable" means that the extracts, cosmetically active agents or inert ingredients which the term describes are suitable for use in contact with tissues (e.g., the skin) without undue toxicity, incompatibility, instability, irritation, allergic response, and the like, commensurate with a reasonable benefit/risk ratio.

As used herein, "regulating the firmness of skin" means the enhancing of the firmness or elasticity of the skin, preventing the loss of firmness or elasticity of skin, or preventing or treating sagging, lax and loose skin. The firmness or elasticity of the skin can be measured by use of a cutometer. See Handbook of Non-Invasive Methods and the Skin, eds. J. Serup & G. Jemec, Chapter 14.3 (1995). The loss of skin elasticity or firmness may be a result of a number of factors, including but not limited to aging, environmental damage, or the result of an application of a cosmetic to the skin.

As used herein, "regulating the tone of skin" means the lightening and/or darkening the skin (e.g., lightening pigmented lesions or darkening skin sallowness).

As used herein, "regulating the texture of skin" means the smoothing of the surface of the skin to remove either bumps or crevasses on the skin surface.

As used herein, "regulating wrinkles in skin" means preventing, retarding, arresting, or reversing the process of wrinkle and fine line formation in skin.

As used herein, "treatment of external aggressions in skin" means the reduction or prevention of the damage from external aggressions in skin. Examples of external aggressions include, but are not limited to, damage to the skin from the use or cleansers (e.g., topical cleansers containing surfactants), make-up, shaving as well as environmental damage such as from UV light (e.g., sundamage from sunlight or damage from non-natural sources such as UV lamps and solar simulators), ozone, exhaust, pollution, chlorine and chlorine containing compounds, and cigarette smoke. Effects of external aggressions on the skin include, but are not limited to, oxidative and/or nitrosative damage to and modifications on lipids, carbohydrates, peptides, proteins, nucleic acids, and vitamins. Effects of external aggressions on the skin also include, but are not limited to, loss of cell viability, loss or alteration of cell functions, and changes in gene and/or protein expression.

As used herein, "safe and effective amount" means an amount of compound or composition (e.g., the Feverfew extract) sufficient to significantly induce a positive modification in the condition to be regulated or treated, but low enough to avoid serious side effects. The safe and effective amount of the compound or composition will vary with the particular condition being treated, the age and physical condition of the end user, the severity of the condition being treated/prevented, the duration of the treatment, the nature of concurrent therapy, the specific compound or composition employed, the particular cosmetically-acceptable topical carrier utilized, and like factors.

Feverfew Extract

What is meant by a "Feverfew extract" is a blend of compounds isolated from a plant from the Chrysanthemum or Tanacetum genus (hereinafter referred to as Feverfew). Examples of Feverfew include, bur are not limited to, Chrysanthemum parthenium, Tanacetum parthenium, or Matricania parthenium, as well as those listed in CRC Ethnobotany Desk Reference 1998, ed. Timothy Johnson, p198-199, 823-824, 516-517 (CRC Press, Boca Raton, Fla., USA 1998) and the 'The Plant Names Project (1999). International Plant Names Index. Published on the Internet; http://www.ipni.org [accessed Jan. 11, 2001].

Such compounds may be isolated from a part(s) of the plant (e.g., the arial part of the plant such as the stem, flower, and leaves) by physically removing a piece of such plant, such as grinding a leaf on the plant. Such compounds may also be isolated from the plant by using extraction procedures well known in the art (e.g., the use of organic solvents such as $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, and/or inorganic solvents such as water, inorganic acids such as hydrochloric acid, and inorganic bases such as sodium hydroxide). In one embodiment, the Feverfew extract contains only hydrophilic compounds (e.g., isolated by using a hydrophilic solvent, such as water or ethanol). In one embodiment, the Feverfew extract contains only hydrophobic compounds (e.g. isolated by using a hydrophobic solvent, such as chloroform). In one embodiment, the Feverfew extract contains both hydrophilic and hydrophobic compounds.

In one embodiment, the Feverfew extract is substantially free of alpha-unsaturated gamma-lactones. The term "substantially free of alpha-unsaturated gamma-lactones," refers to an extract of feverfew having a weight content of the alpha-unsaturated gamma-lactones of less than about 0.2% by weight. These alpha-unsaturated gamma-lactones include, but are not limited to, parthenolide, 3-β-hydroxy-parthenolide, costunolide, 3-β-constunolide, artemorin, 8-α-hydroxy-estafiatin, chysanthemolide, magnoliolide, tanaparthin, tanaparthin-1α,4α-epoxide, tanaparthin-1β,4β-epoxide, chrysanthemonin, and other sesquiterpenes. Preferably, the feverfew extract has a weight content of alpha-unsaturated gamma-lactones below about 0.02% by weight.

Alpha-unsaturated gamma-lactones, including parthenolide, are present in Feverfew. Methods for the manufacture of Feverfew extracts that are substantially free of parthenolide and other alpha-unsaturated gamma-lactones are disclosed in PCT Patent Application No. WO 00/74695.

The amount of the Feverfew extract present in the composition will depend on the type of extract used. In one embodiment, the composition comprises a safe and effective amount of said Feverfew extract. The extract typically will be present in the composition in an amount from about 0.001% to about 20% by weight, in particular in an amount from about 0.01% to about 1% by weight.

The Feverfew extract may contain the following compounds: flavanoid/flavone compounds which include, but are not limited to, tanetin, 3,7,3'-trimethoxyquercetagetin, apigenin and its derivatives. When flavanoid/flavone compounds are present, they are present at a concentration of between about 0.001% to about 0.5% such as between about 0.005% and 0.2% based on the weight of the topical composition.

Topical Compositions

The topical compositions useful in the present invention involve formulations suitable for topical application to skin. In one embodiment, the composition comprises the Feverfew extract and a cosmetically-acceptable topical topical carrier. In one embodiment, the cosmetically-acceptable topical carrier is from about 50% to abut 99.99%, by weight, of the composition (e.g., from about 80% to about 95%, by weight, of the composition.

In one embodiment, the composition is substantially free of parthenolide. What is meant by "substantially free of parthenolide" is that the composition comprises, by weight, less than 0.1%, preferably below 0.01%, more preferably below 0.001% or does not comprise any parthenolide. In one embodiment, the composition does not comprise parthenolide.

The compositions may be made into a wide variety of product types that include but are not limited to lotions, creams, gels, sticks, sprays, shaving creams, ointments, cleansing liquid washes and solid bars, shampoos, pastes, powders, mousses, shaving creams, wipes, patches, nail lacquers, wound dressing and adhesive bandages, hydrogels, films and make-up such as foundations, mascaras, and lipsticks. These product types may comprise several types of cosmetically-acceptable topical carriers including, but not limited to solutions, emulsions (e.g., microemulsions and nanoemulsions), gels, solids and liposomes. The following are non-limitative examples of such topical carriers. Other topical carriers can be formulated by those of ordinary skill in the art.

The topical compositions useful in the present invention can be formulated as solutions. Solutions typically include an aqueous solvent (e.g., from about 50% to about 99.99% or from about 90% to about 99% of a cosmetically acceptable aqueous solvent).

Topical compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., $7^{th}$ Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical compositions useful in the present invention formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, U.S. Pat. Nos. 3,755,560, 4,421,769, McCutcheon's Detergents and Emulsifiers, North American Edition, pp. 317-324 (1986), and the ICI Handbook, pp.1673-1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. Nos. 4,254,105 and 4,960,764, are also useful in the subject invention. In general, such single or multiphase emulsions contain water, emollients, and emulsifiers as essential ingredients.

The topical compositions of this invention can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The topical compositions of the present invention can also be formulated into a solid formulation (e.g., a wax-based stick, soap bar composition, powder, or a wipe containing powder).

Liposomal formulations are also useful compositions of the subject invention. Examples of liposomes are unilamellar, multilamellar, and paucilamellar liposomes, which may or may not contain phospholipids. Such compositions can be prepared by first combining hesperetin with a phospholipid, such as dipalmitoylphosphatidyl choline, cholesterol and water according to the method described in Mezei & Gulasekharam, "Liposomes—A Selective Drug Delivery System for the Topical Route of Administration; Gel Dosage Form", Journal of Pharmaceutics and Pharmacology, Vol. 34 (1982), pp. 473-474, or a modification thereof. Epidermal lipids of suitable composition for forming liposomes may be substituted for the phospholipid. The liposome preparation may then incorporated into one of the above carriers (e.g., a gel or an oil-in-water emulsion) in order to produce the liposomal formulation.

Other compositions and pharmaceutical uses of topically applied liposomes are described in Mezei, M., "Liposomes as a Skin Drug Delivery System", Topics in Pharmaceutical Sciences (D. D. Breimer and P. Speiser, eds.,), Elsevier Science Publishers B. V., New York, N.Y., 1985, pp. 345-358, PCT Patent Application No. WO96/31194 and U.S. Pat. No. 5,260,065.

The topical compositions useful in the subject invention may contain, in addition to the aforementioned components, a wide variety of additional oil-soluble materials and/or water-soluble materials conventionally used in compositions for use on skin, hair, and nails at their art-established levels.

Additional Cosmetically Active Agents

In one embodiment, the topical composition further comprises another cosmetically active agent in addition to the Feverfew extract. What is meant by a "cosmetically active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides such as those disclosed in PCT Patent Application WO00/15188, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera and soy, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited, to glycolic acid, lactic acid, malic acid, salicylic acid, citric acid, and tartaric acid. See, e.g., European Patent Application No. 273,202.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612-13 of the ICI Handbook.

Other Materials

Various other materials may also be present in the compositions useful in the subject invention. These include humectants, proteins and polypeptides, preservatives and an alkaline agent. Examples of such agents are disclosed in the ICI Handbook, pp.1650-1667. The compositions of the present invention may also comprise chelating agents (e.g., EDTA) and preservatives (e.g., parabens). Examples of suitable preservatives and chelating agents are listed in pp. 1626 and 1654-55 of the ICI Handbook. In addition, the topical compositions useful herein can contain conventional cosmetic adjuvants, such as dyes, opacifiers (e.g., titanium dioxide), pigments, and fragrances.

Mineral Water

The compositions of the present invention may be prepared using a mineral water. In one embodiment, the mineral water has a mineralization of at least about 200 mg/L (e.g., from about 300 mg/L to about 1000 mg/L). In one embodiment, the mineral water comprises at least about 10 mg/L of calcium and/or at least about 5 mg/L of magnesium.

The composition and formulations containing such compositions of the present invention may be prepared using methodology that is well known by an artisan of ordinary skill.

EXAMPLE 1

Inhibition of UV Induced MMP

The ability of Feverfew extract to inhibit UV induced matrix metalloproteinase-1 (MMP-1) was evaluated in epidermal equivalents derived from normal human epidermal keratinocytes. MMPs are a family of enzymes that play a major role in physiological remodeling and pathological destruction of extracellular matrix. It is well established that suberythemal doses of UV light induce MMP secretion in human skin, which in turn degrades the extracellular matrix and play a significant role in photoaging wrinkle formation and loss of firmness and elasticity. See G. J. Fisher, et al., Nature 379:335-339 (1996) and G. J. Fisher and J. J. Voorhees, J. Invest. Dermatol. Symposium Proceedings. 3:61-68 (1998).

In order to evaluate the ability of Feverfew extract to inhibit UV induced MMP-1, epidermal equivalents were obtained from SkinEthic (Nice, France), and cultured in phenol free, hydrocortisone free medium (SkinEthic). The equivalents were then topically treated with 0% or 0.5%, by weight, of Feverfew extract (sold as Feverfew Dry Extract D. J. from Indena, S. p. A., Milan, Italy) for 1 to 2 hours prior to irradiating with solar spectrum light at doses of 0, 5, 7, 9 and 11 MED using a 1000 Watt solar ultraviolet simulator (Oriel, Stratford, Conn., USA). Forty-eight hours post-irradiation, the medium below each equivalent was then collected and analyzed for secreted MMP-1 by ELISA (Calbiochem, San Diego, Calif., USA). The results of such experiment are set forth in Table 1.

TABLE 1

| | MMP-1 (ng/ml) | |
|---|---|---|
| UV Light (MED) | 0% Feverfew | 1% Feverfew |
| 0 | 19.3 ± 2.12 | 14.175 ± 1.803 |
| 5 | 28.725 ± 11.561 | 12.575 ± 2.510 |
| 7 | 33.075 ± 4.207 | 15.25 ± 0.495 |
| 9 | 44.000 ± 7.990 | 16.425 ± 7.177 |
| 11 | 28.450 ± 10.041 | 11.075 ± 2.510 |

These results indicate that the formulation containing Feverfew extract was able to provide protection against induction of MMP-1 following irradiation with solar spectrum light up to doses of 11 MED.

EXAMPLE 2

Prevention of Smoke-induced Loss of Thiols

The ability of Feverfew extract to prevent smoke-induced loss of thiols was evaluated in normal human dermal fibroblasts (Clonetics, San Diego, Calif.). Thiols, chiefly glutathione, are part of the endogenous cellular antioxidant defense system. Glutathione serves as a redox buffer, thereby, maintaining the balance between oxidants and antioxidants. Glutathione is also the preferred substrate for several enzymes such as the glutathione peroxidases (decomposing peroxides) and the glutathione-S-transferases (a major group of detoxification enzymes). See, A. Meister, Cancer Res. 54:1969s-1975s (1994).

Cutaneous antioxidants (both enzymatic and non-enzymatic), including glutathione, are depleted after UV or ozone exposure. See, M. J. Connor and L. A. Wheeler, Photochem. Photobiol. 46:239-246 (1987) and R. M. Tyrrell and M. Pidoux, Photochem. Photobiol. 47:405-412 (1988). In cell culture models, low intracellular glutathione (GSH) levels lead to a higher UV radiation sensitivity. Topical application of cysteine derivatives on rat skin has been shown to protect against UV radiation-induced photodamage; this benefit was correlated with an increase in GSH synthesis. See, L. T. van den Broeke and G. M. J. Beijersbergen van Henegouwen, J. Photochem. Photobiol. B Biol. 27:61-65 (1995); K. Hanada, et al., J. Invest. Dermatol. 108:727-730 (1997); and D. P. T. Steenvoorden, et al., Photochem Photobiol. 67:651-656 (1998). Consequently, glutathione is a major endogenous antioxidant, highly responsive to environmental challenges, able to regulate the tone and the wrinkling of skin, as well as treat external aggression.

In this experiment, normal human neonatal dermal fibroblasts seeded in 24-well format Transwell inserts (Corning Costar, Cambridge, Mass.) were incubated with media containing various concentrations Feverfew extract for 24 hours prior to exposure with either placebo (mock) or cigarette smoke (1 cigarette, BASIC Full Flavor 100's cigarettes, Philip Morris, Richmond, Va.) for 10 minutes. Prior to smoke exposure, the medium above the inserts containing the Feverfew extract was removed, and the cells were washed 3 times with Dulbecco's Phosphate-Buffered Saline (Life Technologies, Gaithersburg, Md.) before being smoke-exposed with only media below the inserts. Immediately after exposure, the cells were incubated for another 24-hour period with the previous medium. The cells were washed again, 5 times with Dulbecco's Phosphate-Buffered Saline, and intracellular thiols were then measured by adding 60 μM monobromobimane (Molecular Probes, Eugene, Oreg., USA) to the cells and incubating at 37° C. for 30 minutes before the fluorescence reading. In the presence of thiols, the monobromobimane becomes fluorescent. This fluorescence was measured using a CytoFluor® Fluorescence Plate Reader (PerSeptive Biosystems, Framingham, Mass., USA) set with the following filter combination: excitation at 360 nm and emission at 460 nm.

The results of this experiment are set-forth in Table 2.

TABLE 2

|  | Feverfew extract concentration (μg/ml) | Thiols (Percent of Thiols contained in No Smoke Group; Mean ± S D) |
|---|---|---|
| No Smoke | 0 | 100 ± 12.2 |
| Smoke (10 min.) | 0 | 58.83 ± 7.7 |
|  | 1 | 70.32 ± 16.7 |
|  | 10 | 99.53 ± 12.6 |
|  | 25 | 103.5 ± 4.8 |

These results indicate that a Feverfew extract afforded a protection against smoke-induced loss of thiols (data represent 8 to 9 replicates from 2 independent experiments).

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of enhancing the firmness or elasticity of or retarding the process of wrinkle or fine line formation in skin, said method comprising the topical administration to skin in need of such treatment a composition comprising:

(a) a safe and effective amount of a feverfew extract; and
(b) a cosmetically-acceptable topical carrier, wherein said composition comprises less than 0.1% by weight of parthenolide.

2. A method of claim 1, wherein said method is for enhancing the firmness or elasticity of skin in need of such treatment.

3. A method of claim 1, wherein said method is for retarding the process of wrinkle or fine line formation in skin in need of such treatment.

4. A method of claim 2, wherein said composition comprises from about 0.001%, by weight, to about 20%, by weight, of said feverfew extract.

5. A method of claim 3, wherein said composition comprises from about 0.001%, by weight, to about 20%, by weight, of said feverfew extract.

6. A method of claim 4, wherein said composition comprises from about 0.01%, by weight, to about 1%, by weight, of said feverfew extract.

7. A method of claim 5, wherein said composition comprises from about 0.01%, by weight, to about 1%, by weight, of said feverfew extract.

8. A method of claim 2, wherein said composition comprises less than 0.01%, by weight of parthenolide.

9. A method of claim 3, wherein said composition comprises less than 0.01% by weight of parthenolide.

10. A method of claim 6, wherein said composition comprises less than 0.01% by weight of parthenolide.

11. A method of claim 4, wherein said composition comprises less than 0.01% by weight of parthenolide.

12. A method of claim 7, wherein said composition comprises less than 0.01% by weight of parthenolide.

13. A method of claim 5, wherein said composition comprises less than 0.01% by weight of parthenolide.

* * * * *